(12) United States Patent
Mikhail et al.

(10) Patent No.: US 11,786,125 B2
(45) Date of Patent: Oct. 17, 2023

(54) IMPLANTABLE SENSOR ELECTRONICS PACKAGING

(71) Applicant: DuPuy Synthes Products, Inc., Raynham, MA (US)

(72) Inventors: George Mikhail, Chester Springs, PA (US); Binh Vu, Thorndale, PA (US); Jochen Walser, Ostermundigen (CH); Dan Dlugos, Middletown, OH (US); Mark Fichman, Eindhoven (NL); Seulki Lee, Eindhoven (NL); Navid Shahriari, Weert (NL); Erfan Sheikhi, Eindhoven (NL); Maria Op de Beeck, Leuven (BE)

(73) Assignees: DEPUY SYNTHES PRODUCTS, INC., Raynham, MA (US); STITCHTING IMEC NEDERLAND, Eindhoven (NL); IMEC VZW, Leuven (BE)

( * ) Notice: Subject to any disclaimer, the term of this patent is extended or adjusted under 35 U.S.C. 154(b) by 353 days.

(21) Appl. No.: 17/123,101

(22) Filed: Dec. 15, 2020

(65) Prior Publication Data

US 2022/0183558 A1 Jun. 16, 2022

(51) Int. Cl.
*A61B 5/00* (2006.01)
*A61B 90/00* (2016.01)
(Continued)

(52) U.S. Cl.
CPC .......... *A61B 5/0031* (2013.01); *A61B 5/1036* (2013.01); *A61B 17/80* (2013.01); *A61B 90/06* (2016.02); *A61B 2090/064* (2016.02)

(58) Field of Classification Search
CPC ...... A61N 1/36125; A61N 1/375–3758; A61B 5/0031; A61B 5/1036; A61B 5/6847; A61B 5/686; A61B 5/6878; A61B 5/4504; A61B 17/80; A61B 2560/0406; A61B 2562/00; A61B 2562/02; A61B 2562/04; A61B 2562/043; A61B 2562/0247;
(Continued)

(56) References Cited

U.S. PATENT DOCUMENTS

| | | |
|---|---|---|
| 4,145,921 A | 3/1979 | Blackwelder |
| 4,281,538 A | 8/1981 | Dudek |

(Continued)

FOREIGN PATENT DOCUMENTS

| | | | | |
|---|---|---|---|---|
| CA | 2773168 A1 | * | 9/2012 | ........... A61B 5/0031 |
| WO | WO2004030514 A2 | | 4/2004 | |

(Continued)

*Primary Examiner* — Catherine B Kuhlman
*Assistant Examiner* — Raymond P Dulman (57) ABSTRACT

An implantable device includes a substrate and protective cover that cooperate to define an enclosed sensor volume. A sealed enclosure is provided within the sensor volume, with an electronic component assembly (ECA) being located within the sealed enclosure. A flexible circuit board assembly (FCBA) is electrically coupled with the ECA through a wall of the sealed enclosure. At least one transducer is provided on the FCBA in contact with the substrate, and the FCBA is held apart from the enclosure via a polymeric spacer provided therebetween. An inert polymer fill is provided within the sensor volume external to the enclosure.

20 Claims, 7 Drawing Sheets

(51) Int. Cl.
*A61B 5/103* (2006.01)
*A61B 17/80* (2006.01)

(58) Field of Classification Search
CPC .... A61B 2562/0252; A61B 2562/0261; A61B 2562/028; A61B 2562/16; A61B 2562/164; A61B 2562/166
See application file for complete search history.

(56) References Cited

U.S. PATENT DOCUMENTS

| | | | |
|---|---|---|---|
| 4,626,041 A | 12/1986 | Harbour | |
| 5,962,792 A | 10/1999 | Kimerer, Jr. | |
| 6,962,088 B2 | 11/2005 | Horiuchi | |
| 7,162,289 B2 | 1/2007 | Shah et al. | |
| 7,552,522 B2 | 6/2009 | Shah et al. | |
| 7,812,416 B2 | 10/2010 | Courcimault | |
| 7,854,172 B2 | 12/2010 | O'Brien et al. | |
| 7,912,525 B2 | 3/2011 | Shah et al. | |
| 8,146,422 B2 | 4/2012 | Stein | |
| 8,278,941 B2 | 10/2012 | Kroh et al. | |
| 8,439,821 B2 | 5/2013 | Stiller et al. | |
| 8,486,070 B2 | 7/2013 | Morgan et al. | |
| 8,661,893 B2 | 3/2014 | Stein et al. | |
| 8,679,186 B2 | 3/2014 | Stein et al. | |
| 8,687,865 B2 | 4/2014 | Wilson et al. | |
| 8,721,643 B2 | 5/2014 | Morgan et al. | |
| 9,308,381 B2 | 4/2016 | Mashiach et al. | |
| 9,357,964 B2 | 6/2016 | Stein et al. | |
| 9,848,497 B2 | 12/2017 | Chang et al. | |
| 9,867,552 B2 | 1/2018 | Rowland et al. | |
| 10,070,535 B2 | 9/2018 | Chang et al. | |
| 10,464,836 B2 | 11/2019 | Ruben et al. | |
| 10,499,822 B2 | 12/2019 | Harvey et al. | |
| 2011/0152725 A1 | 6/2011 | Demir et al. | |
| 2012/0277746 A1 | 11/2012 | Morgan et al. | |
| 2012/0296234 A1 | 11/2012 | Wilhelm et al. | |
| 2016/0198981 A1 | 7/2016 | Demir et al. | |
| 2018/0055444 A1 | 3/2018 | Windolf | |
| 2019/0038214 A1* | 2/2019 | Mikhail | A61B 5/0004 |
| 2020/0062633 A1 | 2/2020 | Ruben et al. | |
| 2020/0146624 A1 | 5/2020 | Flitsch et al. | |
| 2021/0128919 A1* | 5/2021 | Zellmer | A61N 1/3758 |

FOREIGN PATENT DOCUMENTS

| | | | | |
|---|---|---|---|---|
| WO | WO-2010149762 A2 * | 12/2010 | ............ | A61B 5/686 |
| WO | WO-2016004251 A1 * | 1/2016 | ............ | A61B 3/16 |
| WO | WO2020223207 A3 | 11/2020 | | |

* cited by examiner

IMPLANTABLE SENSOR ELECTRONICS PACKAGING

TECHNICAL FIELD

The present disclosure relates generally to an implantable sensor module and method of constructing the same.

BACKGROUND

Tracking of physical disease and healing in humans often involves measuring anatomical properties of a patient's body. However, some measurements, such as those that can only be obtained internally, can be difficult to obtain. More recently, there has been an interest in sensors that can be implanted into a patient's body to track the health of the patient over time. For example, attempts have been made to use one or more strain gauges to track healing in a damaged or fractured bone. The one or more strain gauges are attached to an orthopedic implant that is in turn attached to the damaged or fractured bone. As the bone heals, the bone increasingly shares the load imparted by the patient's body on the orthopedic implant. Thus, the load imparted on the bone increases as the bone heals, while the load imparted on the orthopedic implant decreases. In principle, this change in loading can be measured over time by the one or more strain gauges to track the progress of healing in the bone. The measurement can then be communicated to a device outside of the body that can be accessed by a physician.

SUMMARY

An implantable sensor includes a substrate and protective cover that cooperate to define an enclosed sensor volume. A sealed enclosure is provided within the sensor volume, with an electronic component assembly (ECA) being located within the sealed enclosure. In some embodiments, the sealed enclosure if hermetic and/or has a near-hermetic barrier quality, such as may be provided by different types of glass, quartz, or metal. The sealed enclosure may suitably protect the ECA from any possibility of corrosion and/or may inhibit/eliminate the possibility of ingress or egress of any liquids or other ions between the subject's body and the inner enclosure volume.

A flexible circuit board assembly (FCBA) is electrically coupled with the ECA through a wall of the sealed enclosure. In some embodiments, this is accomplished through a plurality of electrical interconnects that are integrated with and extend through a wall of the enclosure. At least one transducer is provided on the FCBA in contact with the substrate, and the FCBA is held apart from the enclosure via a polymeric spacer provided therebetween. In some embodiments, the transducer is a strain gauge operative to measure an amount of elastic strain present in the substrate. When used in connection with the fixation and monitoring of bone fractures, the substrate may be a bone plate or other bone fixation member. Finally, an inert polymer fill may be provided within the sensor volume external to the enclosure as an additional means of sealing the sensor.

As used herein, the terms "a," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. Each value within a range and the endpoints of a range are hereby all disclosed as separate embodiment.

DETAILED DESCRIPTION

The present technology generally relates to an implantable sensor that maintains a high degree of biocompatibility while also enabling the use of specific monitoring transducers. This technology may be useful, for example, in creating a smart bone plate that may have integral strain sensing while being adapted for long term implantable use within a subject. The present designs utilize multiple barrier layers to create an inert and hermetically sealed sensor module that may be integrated into any implantable device.

The present device may utilize a multi-layer construction whereby an inner containment structure/enclosure is nested within a larger external protective shell. In such a design, complex circuitry and electronics may be housed within the inner enclosure, while more discrete sensing components such as strain transducers may exist outside of the inner housing, while still being protected via the sealed protective shell.

The present designs may include various levels of processing power/complexity, however in a preferred embodiment, the sensor may be devoid of any on-board electrochemical power supply/battery. Instead, in some embodiments, the sensor may be powered by way of a received alternating magnetic field.

Figure 1:
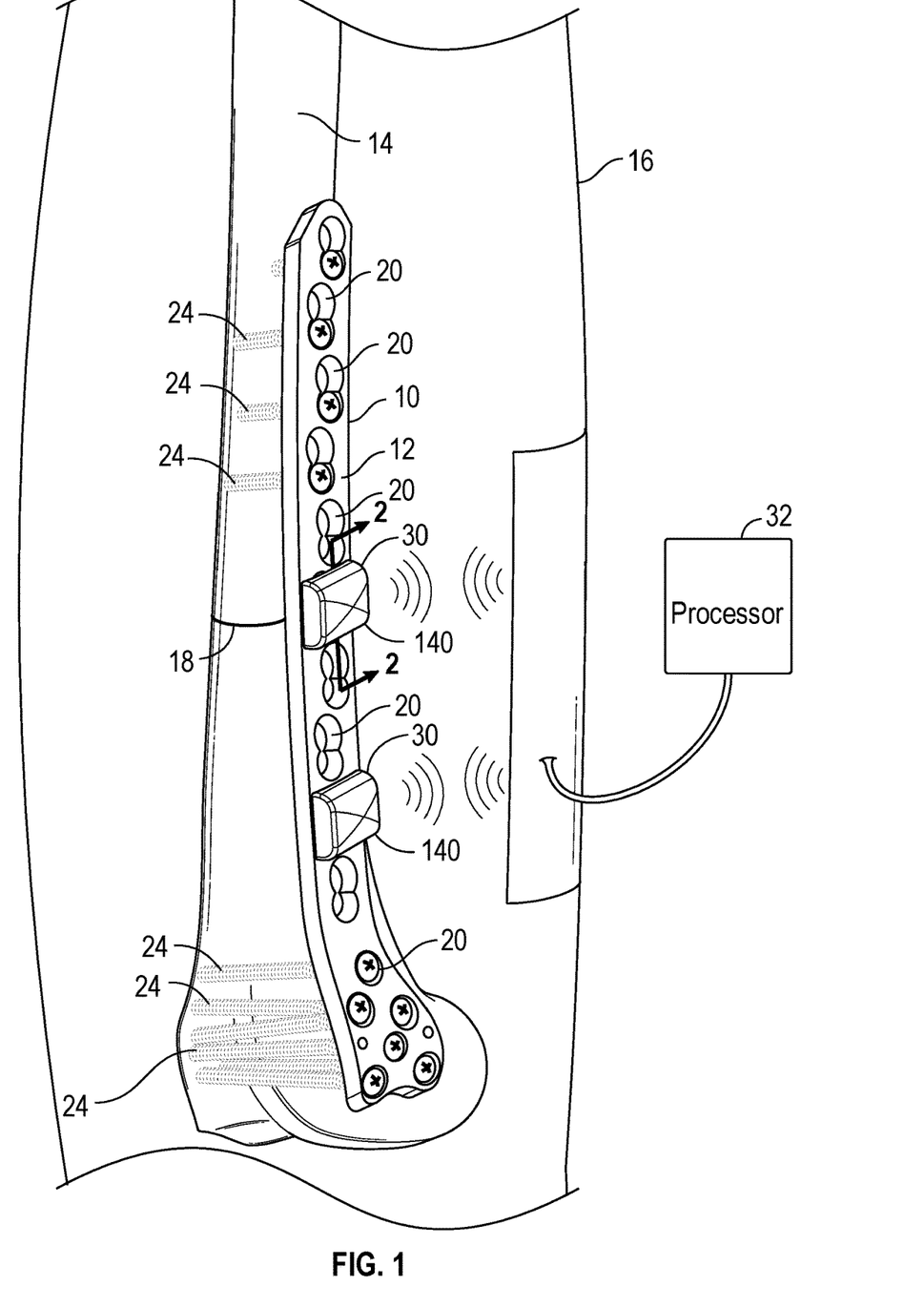
FIG. 1 is a schematic perspective view of an implantable smart fixation device for surgically repairing a fractured bone in communication with an extracorporeal antenna and computing device.

Referring to the figures, FIG. 1 schematically illustrates a smart bone plate 10 according to some embodiments of the present disclosure. The smart bone plate 10 includes a substantially rigid main body 12 that is operative to be secured to a bone 14 of a subject 16 for the purpose of locally fixating a fracture 18 or joint while the fracture heals/ossifies. The main body 12 can be formed from any suitable implantable material such as, without limitation, a metal (e.g., a titanium alloy) or a polymer such as polyether ether ketone (PEEK). The bone plate 10 may include a plurality of apertures 20 that extend through a thickness 22 of the main body 12, where each aperture 20 may be operative to receive a threaded fastener 24 (e.g., a bone screw). The threaded fasteners 24 may be secured or anchored into the bone 14 of the subject 16 to locally attach the main body 12 to the bone 14 on opposing sides of the fracture. The smart bone plate 10 may further include one or more sensor modules 30 that are each operative to sense one or more mechanical parameters of the attached bone plate 10 and communicate these sensed parameters to an external processing device 32.

While the present disclosure generally discusses the sensor design in connection with a bone plate 10, it should be appreciated that the main body 12 of the bone plate 10 is simply an example of a substrate upon which the sensor module 30 may be mounted. Other substrates may similarly be used, including other bone fixation hardware such as pins, rods, intervertebral spacers or cages, or other implantable medical devices where monitoring a mechanical parameter of the device may be beneficial.

Figure 2:
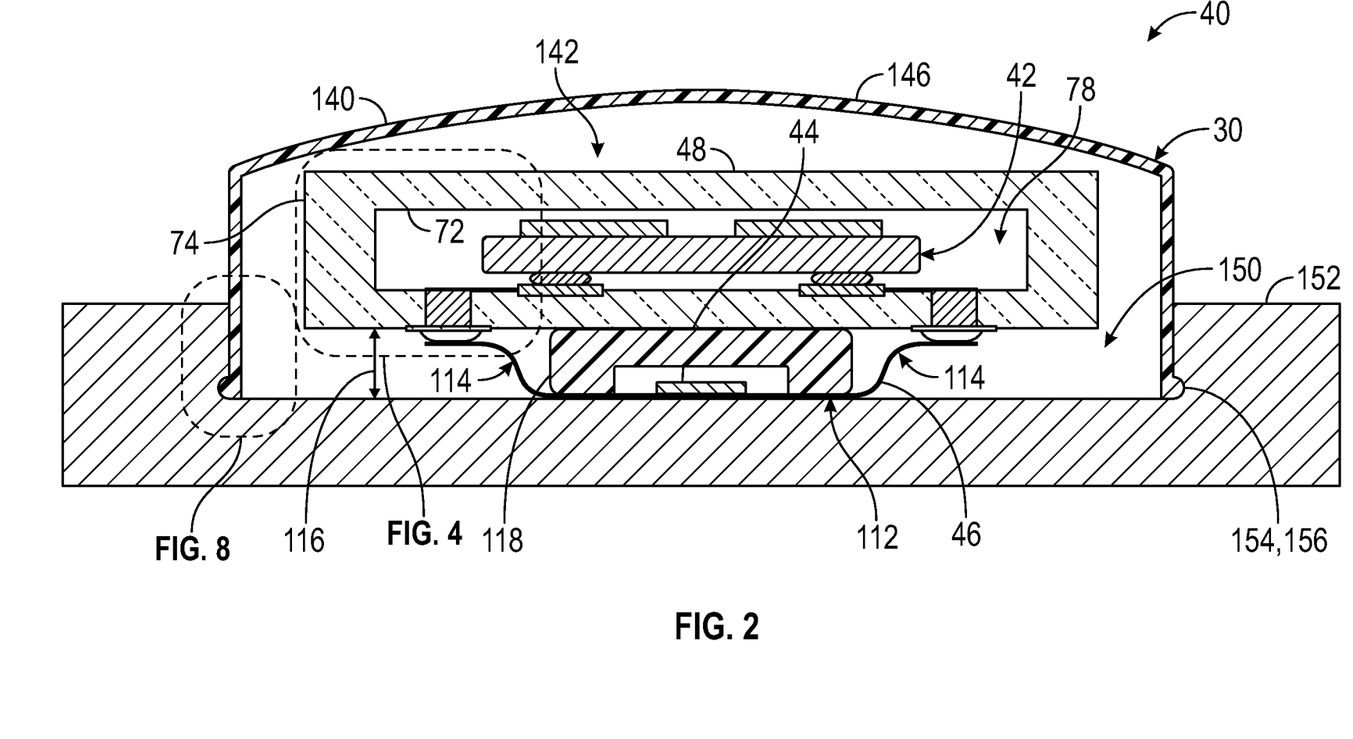
FIG. 2 is a schematic cross-sectional view of a sensor provide on the implantable smart fixation device of FIG. 1, taken along line 2-2.

FIG. 2 provides a schematic cross-sectional view 40 of one of the sensors 30 shown in FIG. 1. As illustrated, the sensor 30 generally includes an electronic component assembly 42 (ECA 42) that is in electrical communication with one or more transducers 44 provided on a flexible circuit board assembly 46 (FCBA 46). In general, the ECA 42 may form the primary "intelligence" of the sensor 30, while also being primarily responsible for all input/output to/from the sensor 30. As such, to protect the integrity of the electronics, the ECA 42 may be provided within a sealed enclosure 48, where all electrical communication between the ECA 42 and the transducers 44/FCBA 46 must pass through a wall of the enclosure 48.

Figure 3:
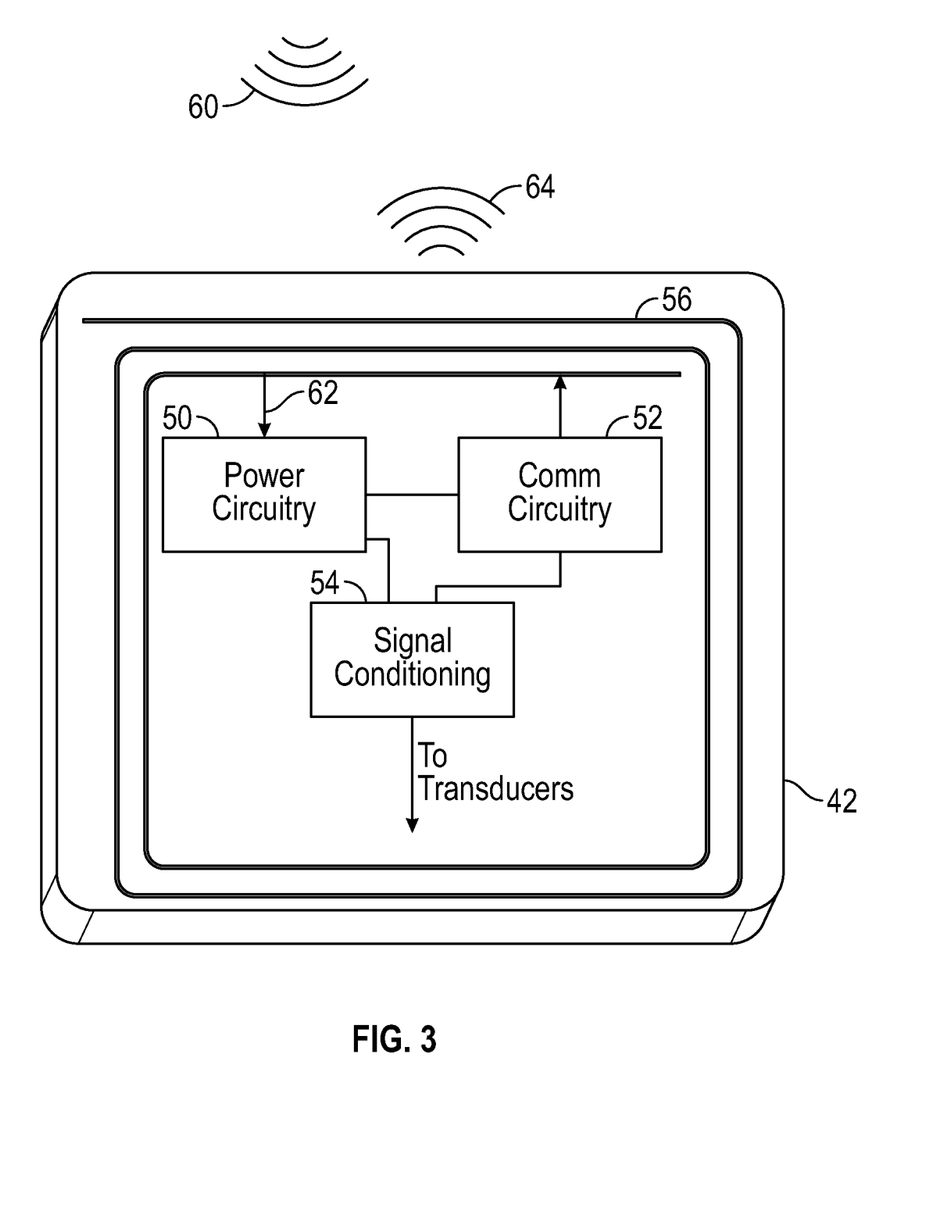
FIG. 3 is a schematic diagram of an electronic component assembly such as may be used with the sensor of FIG. 2.

In general, the ECA 42 may include any combination of one or more active or passive electrical components or integrated circuit packages that are mounted on one or more printed circuit boards/dielectric substrates, or that are mounted directly on a wall of the sealed enclosure 48. Functionally speaking, and as schematically shown in FIG. 3, the ECA 42 may include power circuitry 50, data communication circuitry 52, signal conditioning circuitry 54, and in many embodiments, may further include an antenna 56.

The power circuitry 50 may generally be operative to provide a usable source of electrical power to the transducers 44 and other electrical components within the ECA 42. In at least some examples, the power circuitry 50 can include an energy harvesting device configured to capture energy from a suitable energy source that is separate from the bone plate 10. For example, the energy source can be magnetic fields or radio waves communicated from the external processing device 32 (and/or an antenna associated therewith). Alternatively, the power circuitry 50 can capture energy from the patient's body itself or from another external source such as a source external to the patient's body. More broadly speaking, the energy source can include (without limitation) sensed kinetic energy, electric fields, magnetic fields, and so on. In a preferred embodiment, however, the power circuitry 50 does not include a typical electrochemical battery.

In one particular configuration, instead of relying on an internal store of power, such as an electrochemical battery, the sensor module 30 may be inductively powered by a received magnetic flux/electromagnetic field 60 that may induce a current 62 in the antenna 56. The power circuitry 50 may receive this current from the antenna 56, may rectify and/or regulate it, and may make it available for use by other components within the sensor 30.

The signal conditioning circuitry 54, if included, may comprise one or more signal filters, including a high pass, low pass, and/or band pass filter, one or more digital filters implemented in the frequency domain, or any other required buffering and/or amplifying electronics to make use of the output from the one or more transducers. The signal conditioning circuitry 54 may comprise, for example, one or more RC circuit elements, one or more operational amplifiers, and/or one or more integrated circuit packages.

Finally, the data communications circuitry 52 may serve to receive the output from the transducers 44 and/or signal conditioning circuitry 54 (or a signal representative thereof), and communicate the underlying signal content to the external processing device 32 via an electromagnetic/radio frequency signal 64 that is broadcast from the antenna 56. The communication circuitry 52 may include any/all electronic components that may be required to achieve this functionality as is understood in the art. For example, the communication circuitry 52 can include a wireless transmitter or transponder that receives the measurement value and prepares the measurement value for wireless transmission. The communication circuitry 52 can also include processing components such as (without limitation) one or more of (i) memory configured to store the measurement value, (ii) a digital-to-analog converter configured to convert the measurement value to analog format, (iii) a radio-frequency (RF) modulator configured to modulate the measurement value, (iv) an error-correction encoder configured to encode the measurement value, and other processing consistent with the wireless technology employed by the system.

In one particular configuration, the power circuitry 50 and communication circuitry 52 may be integrated into a single device or package, such as a passive or active RFiD component. In such an embodiment, the power circuitry 50 and communication circuitry 52 may work in tandem to receive the ambient electromagnetic field 60 and output a corresponding electromagnetic signal 64 having a parameter that varies with changes in the output of the one or more transducers 44 (e.g., the transmitted signal 64 may simply be a phase shifted version of the received field 60, with the phase shift being proportional to the output of the transducer 44). In other embodiments, however, there may be greater independence between the power circuitry 50 and communications circuitry 52, where the power circuitry 50 simply acts as a generic power supply to the communication circuitry.

Referring again to FIG. 2, and as noted above, the ECA 42 may be provided within a sealed enclosure 48 that may serve as an environmental barrier and may protect the electronics from corrosion or degradation. In a preferred embodiment, the sealed enclosure 48 may surround the ECA 42 and may be formed from one or more materials that have low or no permeability to liquid and low or no gas or ion diffusion rates and may further have low or no electrical conductivity. Suitable materials may include crystalline materials such as glass, quartz, ceramics, various epoxies, liquid crystal polymer, and the like, or may include metallic materials that have been treated/anodized to reduced surface electrical conductivity. In one particular example, the material used to form the sealed enclosure may comprise a borosilicate glass with a boric oxide concentration of between 10% and 15% by mass. In still other embodiments, the enclosure may comprise a laminate material that includes at least one barrier layer formed from a material with low or no permeability to liquid and low or no gas or ion diffusion rates. For example, the enclosure may be formed from a biocompatible material, such as polyether ether ketone (PEEK), with an inner, outer, or intermediate layer formed from metallic or other barrier-type material using a technique such as atomic layer deposition or the like.

Figure 4:
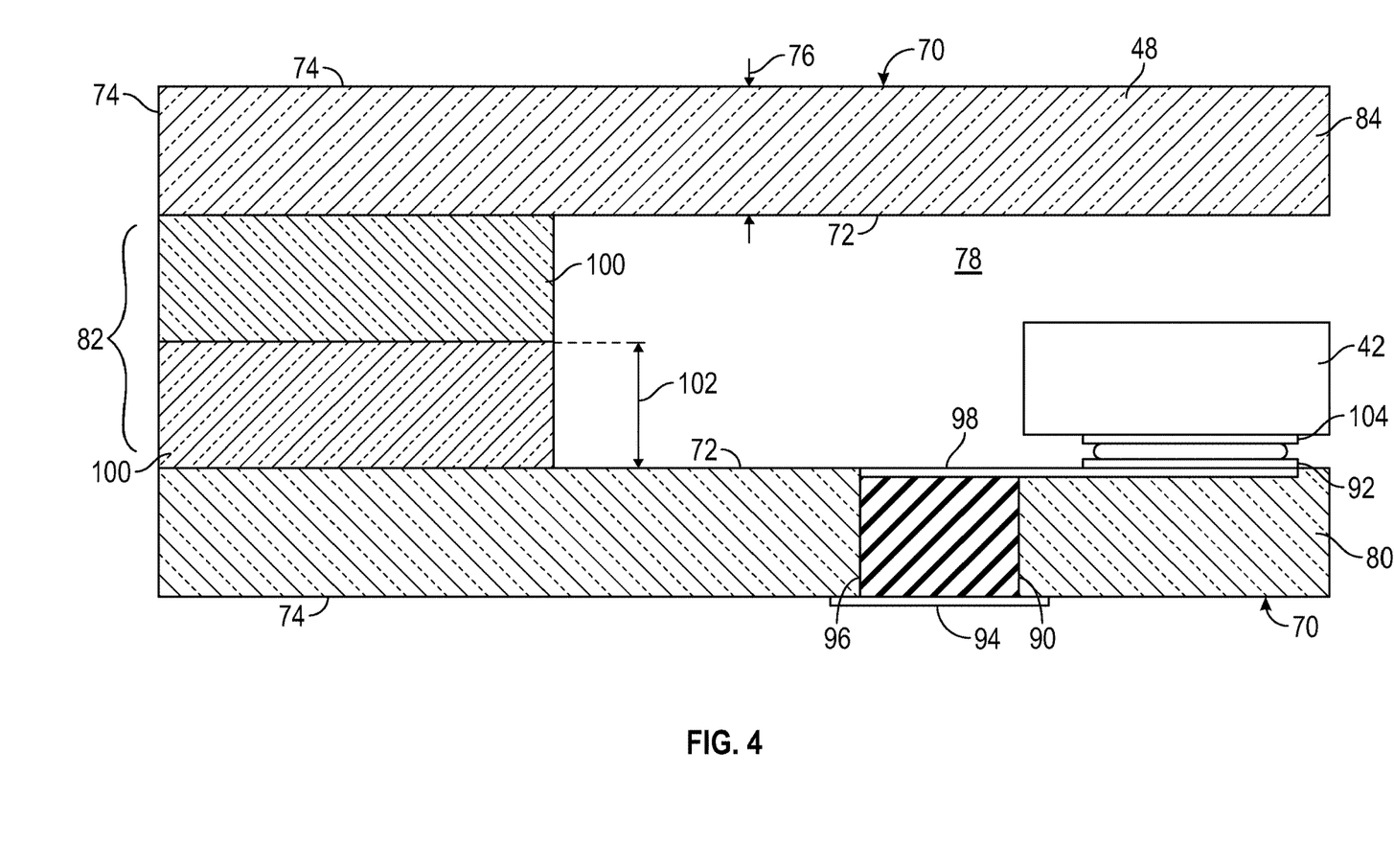
FIG. 4 is an enlarged schematic partial cross-sectional view of the region of FIG. 2 referenced as FIG. 4.

As generally shown in FIGS. 2 and 4, in one configuration, the sealed enclosure 48 may be formed from a plurality of walls 70, each having a corresponding inner surface 72, outer surface 74, and thickness 76 defined between the inner and outer surfaces 72, 74. In one embodiment, the wall thickness 76 may be between about 300 µm and about 800 µm, or between about 400 µm and about 600 µm, or about 500 µm. The inner surfaces 72 of each of the plurality of walls 70 may collectively define an inner enclosure volume 78, within which the ECA 42 may be located. In one configuration, the sealed enclosure 48 may include a base 80, a plurality of side-walls 82, and a cap 84. Each of the base 80, sidewalls 82, and cap 84 may be formed from a similar material, and may be integrally formed with each other and/or may be fused/welded through a suitable manufacturing process.

As generally shown in FIG. 2, and with more clarity in FIG. 4, the base 80 may include a plurality of electrical interconnects 90 or vias that each extend through the thickness 76 of the base 80 from the inner surface 72 to the outer surface 74. Each interconnect/via 90 may be fluidly sealed to the surrounding material of the base 80 and may generally include an inner solder pad 92 provided on the inner surface 72, and outer solder pad 94 provided on the outer surface 74, and a metallic post 96 extending therebetween to electrically couple the inner solder pad 92 with the outer solder pad 94. In one particular configuration, one or more inner solder pads 92 may be physically offset from its corresponding metallic post 96 along the inner surface 72. In such an embodiment, the inner solder pad 92 may be electrically coupled to the corresponding metallic post 96 via one or electrical traces 98 or wires provided on or below the inner surface 72. Such a design may accommodate ECA packaging that may be smaller than the preferred spacing of the outer solder pads 94. Similarly, in some embodiments one or more of the outer solder pads 94 may be physically offset from its corresponding metallic post 96 along the outer surface 74. In such a design, the outer solder pads 94 may be electrically coupled to the corresponding metallic post 96 via one or electrical traces or wires provided on or below the outer surface 74.

As further shown in FIG. 4, in one configuration, the side walls 82 may be formed from a plurality of layers 100 that are arranged in a stacked assembly. In this design, each layer 100 may have an approximately equal layer thickness 102, which also may be approximately equal to the thickness 76 of the cap 84 and/or base 80. Adjacent layers may by fused through the use of, for example, an applied heat treatment or laser welding.

For the purpose of electrically interconnecting with other components, the ECA 42 may generally include one or more surface mount electrical pads 104 that when assembled may match with and may be directly soldered to the inner solder pads 92 of the electrical interconnects 90.

As noted above, the one or more transducers 44 may be external to the sealed enclosure 48 so that they may more accurately experience and monitor the intended mechanical parameter. Furthermore, to prevent the rigid enclosure 48 from influencing the output of the transducers 44, it may also be preferable for the transducers to not be directly mounted to the enclosure 48 itself. To accomplish these design goals, in one embodiment, such as shown in FIGS. 5-6, the transducers 44 may be mounted on a flexible membrane (the FCBA 46) that is external to the enclosure 48 and in electrical communication with the ECA 42 through a wall 70 of the sealed enclosure 48.

In a primary use, the one or more transducers 44 may comprise one or more strain gauges 110 that are operative to sense an experienced elastic strain in the main body 12 of the bone plate 10. In response to the sensed strain, the one or more transducers 42/strain gauges 110 may modulate an electrical parameter that is provided to the ECA 42. In one configuration, each strain gauge 110 may have a resistance that varies in a predictable and repeatable way in response to an experienced strain. In another embodiment, each strain gauge 110 may be a reactive/piezoelectric material whereby experienced strain induces an electrical potential across two terminals. Other transducers, such as thermal transducers/thermocouples, may also be incorporated or used without departing from the spirit of the present disclosure.

In one particular configuration, the one or more strain gauges 110 may comprise a plurality of strain gauges 110 that are each provided at a different respective orientation on the FCBA 46. More specifically, each strain gauge 110 may have a primary sensing axis and/or longitudinal centerline. The primary sensing axis for each strain gauge 110 may be provided at an angle on the FCBA 46 that is not parallel to the primary sensing axis of any other strain gauge 110. In one particular configuration, each strain gauge 110 may have a primary sensing axis that is angularly offset from every other primary sensing axis by an angle that is an integer multiple of 30 or 45 degrees. Further disclosure of examples of sensing electronics that may be used with the present packaging designs are provided in US 2019/0038214, which is incorporated by reference in its entirety and for all purposes.

Figure 5:
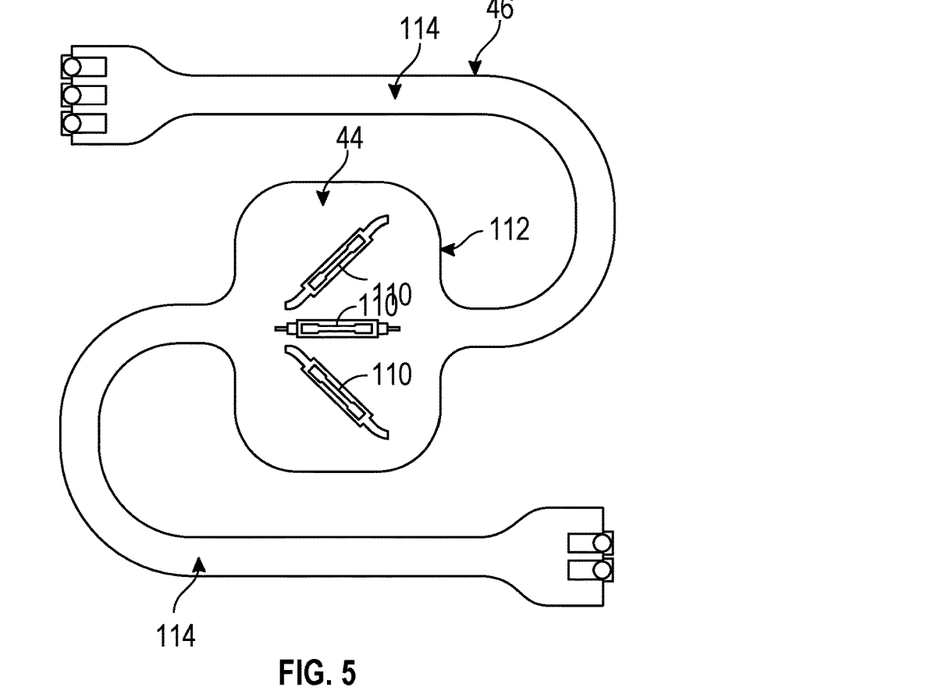
FIG. 5 is a schematic plan view of a flexible circuit board assembly.
Figure 6:
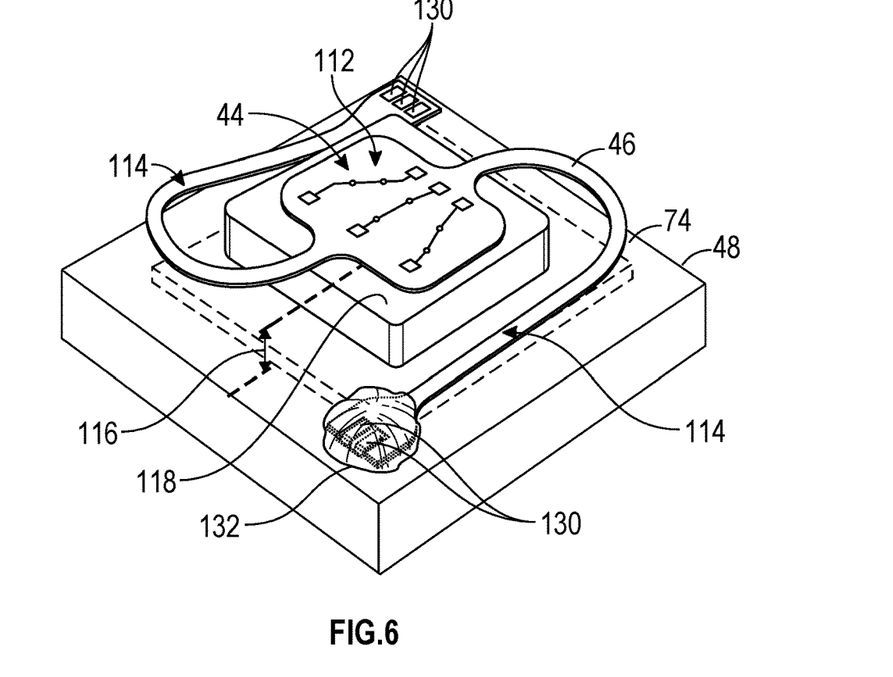
FIG. 6 is a schematic bottom perspective view of an implantable sensor such as shown in FIG. 2.

With reference to FIGS. 2, 5, and 6, in one configuration, the FCBA 46 may generally comprise a sensor portion 112 and one or more connector portions 114. The plurality of transducers 44 may be mounted on the sensor portion 112, while the one or more connector portions 114 may electrically couple the transducers 44 with the electrical interconnects 90 provided on the enclosure 48. As noted above, to maintain some degree of mechanical isolation from the enclosure, the sensor portion 112 may be maintained some minimum distance 116 away from the enclosure 48. As further shown in FIG. 5, the sensor portion 112 and the connector portion 114 may both be formed from the same flexible sheet, where the geometry of the connector portion 114 may facilitate a transverse separation of the sensor portion 112 from the enclosure 48. For example, in one configuration, the connector portion 114 may have a geometry similar to that of a ribbon cable which may roll backward 180 degrees over the edge of the sensor portion 112. Alternatively, as shown in FIGS. 5-6, the connector portion 114 may have a geometry similar to that of a staircase which may double back on itself to minimize the slope of the bend.

The minimum distance 116 between the sensor portion 112 of the FCBA 46 and the outer surface 74 of the sealed enclosure may be maintained, for example, through the use of a flexible spacer 118. In one configuration, the spacer 118 may be formed from a compliant polymer, such as silicone, and may have a transverse thickness, measured between the FCBA 46 and the outer surface 74 of the base 80 of the enclosure 48, of between about 1.0 mm and about 20.0 mm or between 2.0 mm and about 15.0 mm, or between 2.0 mm and about 10.0 mm. The material used to form the spacer 118 may have a hardness, measured on the Shore A scale, of between about 35A and about 65A, or between about 45A and about 55A, or about 50A, and in one embodiment may comprise an injection molded silicone, such as sold under the name NuSil MED-4850, commercialized by Avantor, Inc. In one configuration, the flexible spacer 118 may have a hollow central portion and/or a concave recess on the side in contact with the sensor portion 112 of the FCBA 46. Such a design may aid in maintaining adequate separation between the sealed enclosure 48 and the sensor portion 112 of the FCBA 46/transducers 44, while further reducing any influence that the spacer 118, itself, may have on the sensor readings.

Figure 7:
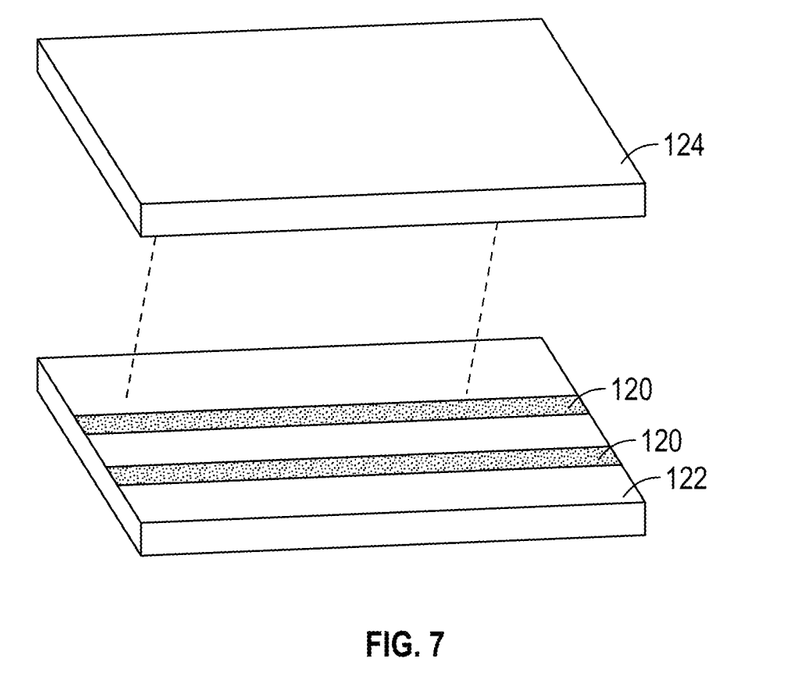
FIG. 7 is a schematic exploded view of a flexible circuit board assembly constructed as a laminate of multiple sheets of liquid crystal polymer

To further the biocompatibility of the present device, in some configurations, the flexible membrane of the FCBA 46 may be formed from a polyimide or liquid crystal polymer material. For example, as generally illustrated in FIG. 7, a plurality of electrically conductive, traces/conductors 120 may be provided on a first sheet 122 of LCP, whereafter a second sheet 124 of LCP may be overlaid on top of the traces 120 (thus sandwiching the traces 120 between the two layers 122, 124). Following this, the adjacent layers 122, 124 of LCP may be thermally fused together and/or heated to a point where the polymer may reflow and solidify as a single thickness of material. While an FCBA 46 with only two layers is shown in FIG. 6, more than two layers of LCP may be used with traces 120 included between any or all adjacent layers.

As generally illustrated in FIG. 6, the FCBA 46 may be electrically coupled to the outer solder pads 94 of the sealed enclosure via one or more solder joints 130. While solder provides excellent electrical connectivity, lead-free solder formulations have especially poor mechanical strength. As such, to insulate and protect the solder joints 130, made between the FCBA 46 and the outer solder pads 94 on the sealed enclosure 48, each solder joint 130 may be covered with a biocompatible epoxy 132. This may provide both a mechanical resiliency to the joint 130, and may provide a further environmental barrier around the material of the joint itself.

In one configuration, a similar epoxy may also be used to hold the sensor portion 112, including the transducers 44, in substantially rigid contact with the main body 12 of the bone plate 10. Ideally, the epoxy selected to adhere the FCBA 46 to the main body 12 should be sufficiently rigid to ensure continuous contact while being flexible enough to not significantly affect the monitored mechanical parameter In some embodiments, following assembly, the FCBA 46 and sealed enclosure 48 may both be coated in an inert barrier material to provide enhanced biocompatibility and environmental protection. Such a coating may be applied, for example, using a deposition process (e.g., atomic layer deposition (ALD), plasma layer deposition (PVD), chemical layer deposition (CVD), or the like). In this process, the assembly may be coated with a barrier material such as, for example, a deposited metal oxide (e.g., $AL_2O_3$, $TiO_2$, $HfO_2$) and/or a barrier polymer. In some embodiments, the barrier material may comprise a laminate that alternates one or more different metallic oxide layers and/or one or more polymer layers. For example, in one particular configuration, the barrier material may comprise a laminate formed by alternating layers of hafnium oxide and aluminum oxide. In another configuration, the barrier material may comprise a laminate that alternates layers of a metal oxide laminate (e.g., $HfO_2$—$Al_2O_3$—$HfO_2$) with one or more layers of a polymer (e.g., Parylene). One particular embodiment of this configuration may include at least three layers of the oxide laminate, and at least two layers of the polymer in an alternating configuration. In some embodiments the barrier layer may have an average thickness of between about 10 nm and about 150 nm.

Referring again to FIGS. 1-2, as a final layer of mechanical and fluidic protection for the enclosed electronics, a protective cover 140 may surround the sealed enclosure 48 and FCBA 46. The protective cover 140 may be coupled to the main body 12 of the bone plate 10 to define a sensor volume 142 therebetween. In some embodiments, any space within the sensor volume 142 that is not filled by the sealed enclosure 48 or FCBA 46 may be filled with a biocompatible polymer such as silicone during the assembly process. In one configuration, this polymer fill may have a hardness when cured of between about 35A and about 65A, or between about 45A and about 55A, or about 50A, and in one embodiment may comprise a low-viscosity silicone, such as sold under the name NuSil MED-6215, commercialized by Avantor, Inc. In one configuration, the protective cover 140 may include a convex/domed upper surface 146 to provide improved impact resistance. Likewise, the cover 140 may be formed from a biocompatible material such as PEEK.

Figure 8:
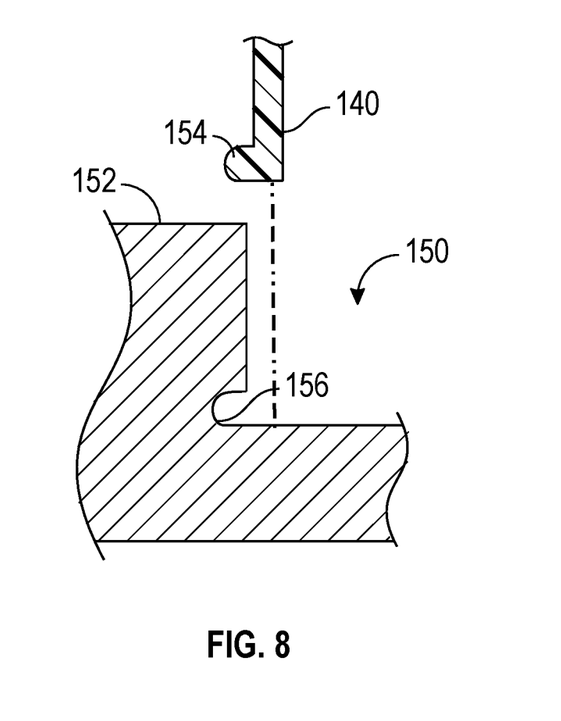
FIG. 8 is an enlarged schematic partial cross-sectional view of the region of FIG. 2 referenced as FIG. 8.

FIG. 8 schematically illustrates one manner of mechanically attaching the protective cover 140 to the main body 12 of the bone plate 10. As shown, the main body 12 may include a concave recess 150 formed in an outer surface 152. When the protective cover 140 is attached to the main body 12, at least a portion of the cover 140 (i.e., a side opposite the domed upper surface 146) may extend within the recess 150. In one configuration, the protective cover 140 may include a protrusion or other mechanical engagement feature 154 that is configured to interlock with a mating portion of the main body 12 within the recess 150. As shown in FIG. 8, in one configuration, this protrusion may extend radially outward away from the sensor volume 142 and may seat within a concave indent 156 in the wall of the recess 150 to resist the cover 140 from being freely removed from the bone plate 10.

While the above disclosure generally refers to the sealed enclosure 48 as its own entirely enclosed box/container with the ECA 42 being entirely surrounded by the walls of this enclosure 48, in another embodiment, the ECA 42 may form one of the walls of the enclosure and/or one of the walls of the enclosure 48 may be integral to the ECA 42. Slightly restated, the embodiments described above generally consider the ECA 42 to comprise one or more electrical components or integrated circuits mounted to a printed circuit board (PCB), whereby the components and the PCB are surrounded by the enclosure 48 (as illustrated in the figures). In an alternate embodiment, however, the sealed enclosure 48 may include one or more insulated electrical traces directly on or in one or more walls 70. In such a design, the electrical components of the ECA 42 may be mounted on the wall, thus eliminating the need for a separate PCB. In a first variation of this configuration, the wall containing the traces (e.g., the base 80) may be formed from the barrier material much like every other wall. In a second variation, however, the wall containing the traces (e.g., the base 80) may be formed from a first material, while the remaining side walls 82 and cap 84 may be formed from the barrier material. Such a design may require an exterior barrier coating, though may enable the PCB to serve as a wall, which may reduce manufacturing complexity.

In still another embodiment, rather than being a container that has a well-defined interior cavity/volume defined by a plurality of generally plain walls, the sealed enclosure 48 may instead be simply a barrier coating applied to the ECA 42. In such an embodiment, the inner enclosure volume 78 may have an identical, or near identical size as the ECA 42 (i.e., by virtue of it being directly applied to the ECA 42). In such an embodiment, the coating may be a barrier coating such as $Al_3O_2$ or LCP, and may be applied using a suitable coating process such as dip-coating or Atomic Layer Deposition.

As noted above, in some embodiments, the sealed enclosure 48 may be formed from a metallic material. If this metallic material is radio opaque, then placing the antenna 56 within the sealed enclosure 48 would compromise or destroy the wireless functionality of the sensor 30. In such a design, however, the antenna 56 may be provided external to the sealed enclosure 48 and coupled to the ECA 42 through one or more electrical interconnects 90 provided through a wall of the enclosure 48 (i.e., electrical antenna interconnects) though electrically insulated from any electrically conductive walls. In such an embodiment, the antenna 56 may be physically separated from the enclosure 48 by a distance of between about 2.0 mm and about 20 mm. More specifically, about 2.0 mm of physical separation may be required to minimize any RF distortion or interference effects caused by a metallic housing/wall. In such a design, the antenna 56 may be provided on an opposite side of the enclosure 48 from the transducers 44 and/or main body 12 of the bone plate 10.

Figure 9:
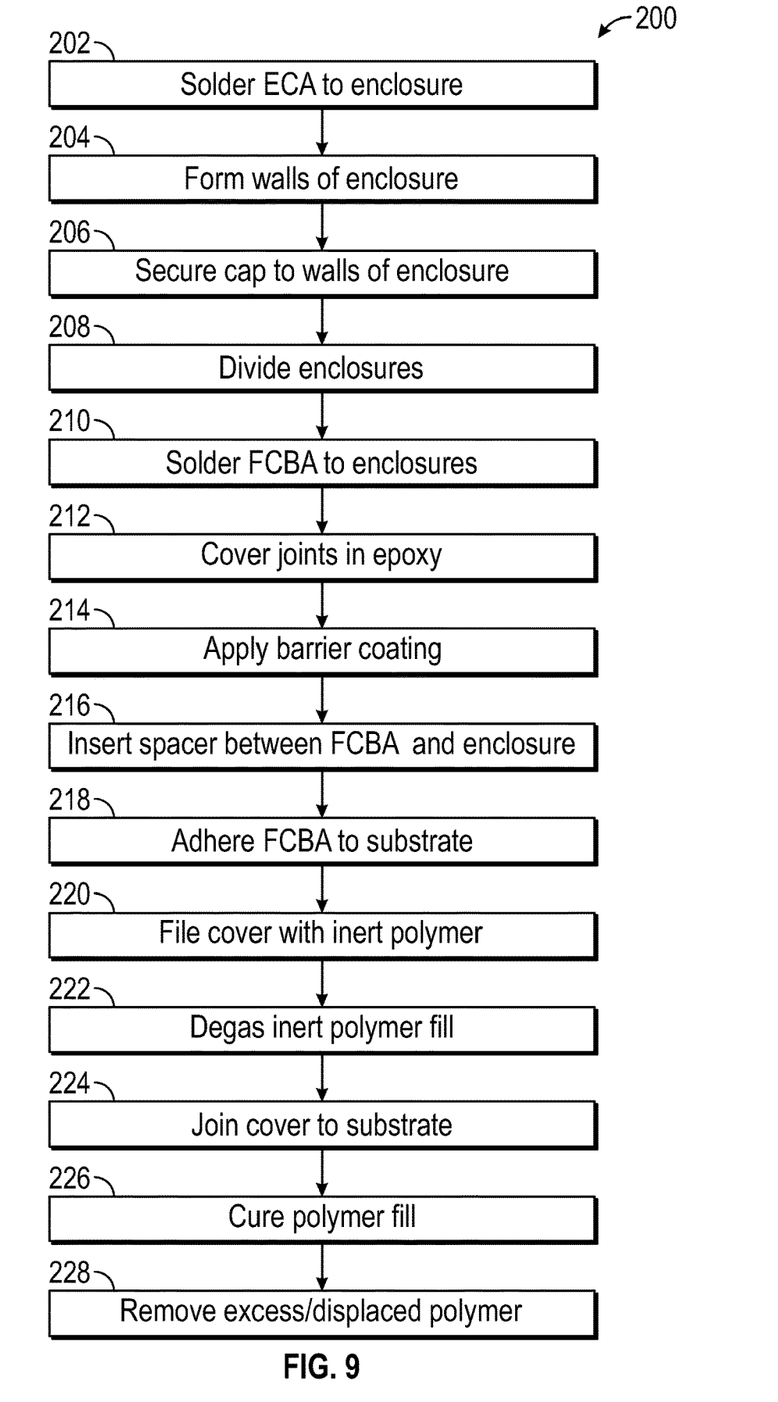
FIG. 9 is a schematic method of manufacturing an implantable sensor.

FIG. 9 schematically illustrates one example of a method 200 for assembling an implantable sensor such as described above with respect to FIGS. 1-8. The method may generally begin at 202 by soldering an electronic component assembly (ECA) to one or more inner solder pads on the inner surface of a base of an enclosure. In one particular embodiment, this soldering step may be performed through an automated process using, for example, a pick and place machine and a solder reflow oven. In one embodiment, a plurality of enclosure bases may be initially joined together as part of a common platter.

Sidewalls for the enclosure may be formed either by etching or otherwise forming recesses into the platter, or by stacking up one or more wall layers on top of the base and subsequently bonding or fusing all adjoining layers together, such as through a laser fusing process (shown at 204, though no order relative to 202 should be implied unless the walls are formed through an etching process—in which case the etching likely need occur prior to the ECA being soldered to the base).

Following the creation of the sidewalls (at 204) and installation of the ECA on the base (at 202), a cap may be secured to the walls (at 206) to fully enclose each ECA within its own inner enclosure volume. In one configuration, the cap may be similar to the base in material and thickness, and in some configurations may also be similar in material and in thickness to the walls (or to each of a plurality of stacked wall layers). The cap may be secured to the walls, for example, by a process such as laser welding.

If a plurality of enclosures are all formed on a common platter, then at 208, the platter may be diced into discrete enclosures. Suitable dicing or cutting processes may be used to separate the enclosures, such as through one or more cutting tools/processes, or through the use of laser energy. In one embodiment, the cutting process may simultaneously weld each of the base, wall layers, and cap together, thus reducing the need to separately affix them.

Once the sealed enclosure is created, terminals or solder pads provided on the flexible circuit board assembly (FCBA) may be soldered to corresponding outer solder pads provided on the outer surface of the sealed enclosure (at 210). Each terminal or solder joint may then be covered in epoxy (at 212) to serve as a barrier layer, but more importantly to provide enhanced mechanical bonding between the FCBA and the enclosure and not simply rely on the mechanical properties of the solder itself. In some embodiments, the sealed enclosure and FCBA may then be coated in barrier layer, for example, using an atomic layer deposition process (at 214).

Following the attachment of the FCBA to the sealed enclosure, a flexible polymeric spacer may be inserted between the sensor portion of the FCBA and the sealed enclosure (at 216). The FCBA may then be epoxied or otherwise adhered to a substrate that is desired to be monitored, such as the main body of a bone plate (at 218).

An injection molded protective cover may then be filled with a low-viscosity inert polymer, such as a silicone (at 220). More specifically, the protective cover may be inverted such that the open end is upward-facing, and the cover resembles a cup. The interior volume of the cover may then be filled with the low-viscosity inert polymer.

Once the cover is filled with the polymer (at 220), the uncured polymer may be degassed (at 222) such as by subjecting the polymer to a negative relative pressure. For example, in one embodiment, the substrate (e.g., the main body of the bone plate) and attached sealed enclosure and FCBA may be positioned, together with the polymer-filled cover, within a vacuum chamber. A vacuum pump may then draw down the ambient air pressure within the vacuum chamber to a level that is below atmospheric pressure and sufficiently low to effect a degassing of the polymer/uncured silicone. Once sufficiently degassed within the chamber (at 222), the cover may be joined with the substrate (at 224) such that the sealed enclosure, flexible spacer, and/or FCBA impresses into the polymer/uncured silicone. In one configuration, the cover may be joined with the substrate by bringing the two components into contact, and further by nesting the cover within a recess in the substrate and/or interlocking a protrusion on one component with a corresponding recess on the other component in a manner that resists withdrawal/removal of the cover from the substrate.

Once joined (at 224), the polymer fill may be cured (at 226), such as through the application of thermal energy/heat and/or by waiting a predetermined amount of time for the material to self-cure. Following the completion of the curing, any displaced/excess polymer fill may be removed (at 228).

Benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are expressly stated in such claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

Additional details and/or embodiments are provided in the following clauses:

Clause 1. An implantable device adapted for use within a living subject, the device comprising: a substrate; a sealed enclosure having a plurality of walls defining an inner enclosure volume therebetween, the sealed enclosure comprising a plurality of electrical interconnects, each electrical interconnect extending through one of the plurality of walls; an electronic component assembly (ECA) provided within the inner enclosure volume, the ECA being electrically coupled to each of the electrical interconnects; a flexible circuit board assembly (FCBA) provided external to the sealed enclosure and in contact with the substrate, the FCBA being electrically coupled to each of the electrical interconnects such that the FCBA is in electrical communication with the ECA through the sealed enclosure, the FCBA further including: at least one transducer operative to monitor a physical characteristic of the substrate and alter an electrical parameter accessible to the ECA in response to the monitored physical characteristic; and a protective cover coupled to the substrate to define an enclosed sensor volume therebetween, and wherein the sealed enclosure and FCBA are both located within the enclosed sensor volume.

Clause 2. The implantable device of clause 1, further comprising a polymeric spacer provided between the at least one transducer and the sealed enclosure, the polymeric spacer having a thickness measured between the sealed enclosure and the FCBA of between about 2.0 mm and 15.0 mm.

Clause 3. The implantable device of any of clauses 1-2, wherein the ECA comprises power circuitry operative to provide a source of electrical energy, and further comprises communications circuitry operative to outwardly communicate one or more data signals from the sensor.

Clause 4. The implantable device of clause 3, further comprising an antenna in electrical communication with both the power circuitry and the communications circuitry; wherein the antenna is operative to receive electromagnetic energy and to provide a corresponding electrical current to the power circuitry; and wherein the antenna is operative to receive an electrical signal from the communications circuitry and to emit a corresponding radio frequency (RF) signal that is representative of the one or more data signals.

Clause 5. The implantable device of clause 4, wherein the sealed enclosure is RF transparent and the ECA further comprises the antenna.

Clause 6. The implantable device of clause 5, wherein the sealed enclosure is formed from glass.

Clause 7. The implantable device of clause 4, wherein the sealed enclosure is radio opaque; and wherein the antenna is provided external to the sealed enclosure.

Clause 8. The implantable device of any one of clauses 1-7, wherein the sealed enclosure is hermetically sealed.

Clause 9. The implantable device of any one of clauses 1-8, wherein the enclosed sensor volume, external to the sealed enclosure, is filled with a polymeric sealant material.

Clause 10. The implantable device of clause 9, wherein the polymeric sealant material is a silicone polymer.

Clause 11. The implantable device of any one of clauses 1-10, wherein the substrate includes a concave recess formed into an outer surface of the substrate; wherein a portion of the FCBA is in contact with the substrate within the recess; and wherein the protective cover includes a mechanical engagement feature that interlocks with the substrate within the recess to resist removal of the cover from the substrate.

Clause 12. The implantable device of any one of clauses 1-11, wherein the substrate is a bone plate that includes a plurality of apertures extending through a main body of the bone plate, each aperture being operative to receive a threaded fastener to affix the main body to a bone of a subject; and wherein the main body is the substrate.

Clause 13. The implantable device of any one of clauses 1-12, wherein the at least one transducer comprises a strain gauge operative to monitor an amount of elastic strain in the substrate.

Clause 14. The implantable device of any one of clauses 1-13, wherein the FCBA and plurality of electrical interconnects are at least partially coated with a barrier material.

Clause 15. The implantable device of clause 14, wherein the barrier material is a liquid crystal polymer.

Clause 16. The implantable device of clause 14, wherein the barrier material is a laminate comprising a plurality of layers of one or more metal oxides; and wherein the barrier layer has an average thickness of between about 10 nm and about 150 nm.

Clause 17. The implantable device of clause 16, wherein the barrier material comprises alternating layers of a metal oxide laminate and a polymer, and wherein the metal oxide laminate comprises at least two layers, each formed from a different metal oxide material.

Clause 18. The implantable device of any one of clauses 1-17, wherein the FCBA comprises a plurality of sheets of liquid crystal polymer and a plurality of electrically conductive traces; and wherein each of the plurality of electrically conductive traces are embedded between adjacent sheets of liquid crystal polymer that are fused together.

Clause 19. The implantable device of clause 1, wherein sealed enclosure comprises a barrier coating provided on the ECA.

Clause 20. A method of manufacturing a biocompatible, implantable sensor, the method comprising: enclosing an electronic component assembly within a hermetically sealed enclosure; electrically coupling a flexible circuitry board assembly (FCBA) to the electronic component assembly through a wall of the enclosure, the FCBA including a transducer provided on a sensing portion of the FCBA; inserting a polymeric spacer between the sensing portion of the FCBA and the base of the enclosure, the polymeric spacer being operative to maintain the sensing portion a predefined minimum distance away from the enclosure; affixing the sensing portion of the FCBA to a substrate; affixing a polymeric cap to the substrate, wherein the polymeric cap and the substrate cooperate to define an inner sensor volume, and wherein the enclosure and FCBA are located within the inner sensor volume.

Clause 21. The method of clause 20, wherein electrically coupling the FCBA to the electronic component assembly comprises: soldering the electronic component assembly to inner solder pads provided on an inner surface of a base of the enclosure; and soldering terminals on the FCBA to outer solder pads provided on an outer surface of the base of the enclosure, the outer solder pads being electrically coupled to the inner solder pads through a thickness of the base.

Clause 22. The method of any of clauses 20-21, further comprising filling the polymeric cap with an uncured inert polymeric material prior to affixing it to the substrate.

Clause 23. The method of clause 22, further comprising curing the inert polymeric material after affixing the polymeric cap to the substrate.

Clause 24. The method of clause 23, further comprising subjecting the cap to a negative relative pressure, compared to ambient pressure, to effect a degassing of the uncured inert polymeric material prior to affixing the polymeric cap to the substrate.

Clause 25. The method of any of clauses 20-24, wherein affixing the polymeric cap to the substrate includes inserting a portion of the cap into a recess formed into the substrate.

Clause 26. The method of clause 25, wherein affixing the polymeric cap to the substrate further includes interlocking a protrusion on one of the cap or the substrate with a corresponding recess on the other of the cap or the substrate to resist withdrawal of the cap from the substrate.

Clause 27. The method of any of clauses 20-26, further comprising applying an epoxy to surround the terminals on the FCBA and mechanically couple the FCBA to the enclosure.

Clause 28. The method of any of clauses 20-27, further comprising forming the enclosure by: a plurality of sidewalls on a base of the enclosure; and securing a cap to the plurality of sidewalls.

Clause 29. The method of clause 28, wherein forming sidewalls of the enclosure on the base comprises stacking a plurality of layers of material on the base; and fusing each of the plurality of layers and the base together using a laser.

Clause 30. The method of clause 29, further comprising fusing the cap to the sidewalls using a laser.

Clause 31. The method of clause 30, wherein each of the base, plurality of walls, and cap are formed from a glass material having a boric oxide concentration of between 10% and 15% by mass.

Clause 32. The method of any of clauses 20-31, wherein affixing the sensing portion of the FCBA to the substrate comprises affixing the sensing portion of the FCBA to the main body of a bone plate, and wherein the transducer is a strain gauge.

The invention claimed is:

1. An implantable device adapted for use within a living subject, the device comprising:
    a substrate;
    a sealed enclosure having a plurality of walls defining an inner enclosure volume therebetween, the sealed enclosure comprising a plurality of electrical interconnects, each electrical interconnect extending through one of the plurality of walls;
    an electronic component assembly (ECA) provided within the inner enclosure volume, the ECA being electrically coupled to each of the electrical interconnects;
    a flexible circuit board assembly (FCBA) provided external to the sealed enclosure and in contact with the substrate, the FCBA being electrically coupled to each of the electrical interconnects such that the FCBA is in electrical communication with the ECA through the sealed enclosure, the FCBA further including:
        at least one transducer operative to monitor a physical characteristic of the substrate and alter an electrical parameter accessible to the ECA in response to the monitored physical characteristic; and
    a protective cover coupled to the substrate to define an enclosed sensor volume therebetween, and wherein the sealed enclosure and FCBA are both located within the enclosed sensor volume.

2. The implantable device of claim 1, further comprising a polymeric spacer provided between the at least one transducer and the sealed enclosure, the polymeric spacer having a thickness measured between the sealed enclosure and the FCBA of between about 2.0 mm and 15.0 mm.

3. The implantable device of claim 1, wherein the ECA comprises power circuitry operative to provide a source of electrical energy, and further comprises communications circuitry operative to outwardly communicate one or more data signals from the sensor.

4. The implantable device of claim 3, further comprising an antenna in electrical communication with both the power circuitry and the communications circuitry;
    wherein the antenna is operative to receive electromagnetic energy and to provide a corresponding electrical current to the power circuitry; and
    wherein the antenna is operative to receive an electrical signal from the communications circuitry and to emit a corresponding radio frequency (RF) signal that is representative of the one or more data signals.

5. The implantable device of claim 4, wherein the sealed enclosure is RF transparent and the ECA further comprises the antenna.

6. The implantable device of claim 5, wherein the sealed enclosure is formed from glass.

7. The implantable device of claim 4, wherein the sealed enclosure is radio opaque; and
    wherein the antenna is provided external to the sealed enclosure.

8. The implantable device of claim 1, wherein the sealed enclosure is hermetically sealed.

9. The implantable device of claim 1, wherein the enclosed sensor volume, external to the sealed enclosure, is filled with a polymeric sealant material.

10. The implantable device of claim 9, wherein the polymeric sealant material is a silicone polymer.

11. The implantable device of claim 1, wherein the substrate includes a concave recess formed into an outer surface of the substrate;
    wherein a portion of the FCBA is in contact with the substrate within the recess; and
    wherein the protective cover includes a mechanical engagement feature that interlocks with the substrate within the recess to resist removal of the cover from the substrate.

12. The implantable device of claim 1, wherein the substrate is a bone plate that includes a plurality of apertures extending through a main body of the bone plate, each aperture being operative to receive a threaded fastener to affix the main body to a bone of a subject; and
    wherein the main body is the substrate.

13. The implantable device of claim 1, wherein the at least one transducer comprises a strain gauge operative to monitor an amount of elastic strain in the substrate.

14. The implantable device of claim 1, wherein the FCBA and plurality of electrical interconnects are at least partially coated with a barrier material.

15. The implantable device of claim 14, wherein the barrier material is a liquid crystal polymer.

16. The implantable device of claim 14, wherein the barrier material is a laminate comprising a plurality of layers of one or more metal oxides; and
    wherein the barrier layer has an average thickness of between about 10 nm and about 150 nm.

17. The implantable device of claim 16, wherein the barrier material comprises alternating layers of a metal oxide laminate and a polymer, and wherein the metal oxide laminate comprises at least two layers, each formed from a different metal oxide material.

18. The implantable device of claim 1, wherein the FCBA comprises a plurality of sheets of liquid crystal polymer and a plurality of electrically conductive traces; and
   wherein each of the plurality of electrically conductive traces are embedded between adjacent sheets of liquid crystal polymer that are fused together.

19. The implantable device of claim 1, wherein sealed enclosure comprises a barrier coating provided on the ECA.

20. A method of manufacturing a biocompatible, implantable sensor, the method comprising:
   enclosing an electronic component assembly within a hermetically sealed enclosure;
   electrically coupling a flexible circuitry board assembly (FCBA) to the electronic component assembly through a wall of the enclosure, the FCBA including a transducer provided on a sensing portion of the FCBA;
   inserting a polymeric spacer between the sensing portion of the FCBA and a base of the enclosure, the polymeric spacer being operative to maintain the sensing portion a predefined minimum distance away from the enclosure;
   affixing the sensing portion of the FCBA to a substrate;
   affixing a polymeric cap to the substrate, wherein the polymeric cap and the substrate cooperate to define an inner sensor volume, and wherein the enclosure and FCBA are located within the inner sensor volume.

* * * * *